United States Patent [19]

Larrick et al.

[11] Patent Number: 4,684,623
[45] Date of Patent: Aug. 4, 1987

[54] USE OF TUMOR NECROSIS FACTOR AS A WEIGHT REGULATOR

[75] Inventors: James W. Larrick, Woodside; Gordon M. Ringold, Palo Alto; David F. Mark, Danville; Leo S. Lin, Walnut Creek; Frank M. Torti, Palo Alto, all of Calif.

[73] Assignees: The Board of Trustees of the Cetus Corporation, Emeryvile; Leland Stanford Junior University, Stanford, both of Calif.

[21] Appl. No.: 801,989

[22] Filed: Nov. 26, 1985

Related U.S. Application Data

[63] Continuation-in-part of Ser. No. 730,367, May 2, 1985.

[51] Int. Cl.[4] .................... A61K 37/02; A61K 39/00
[52] U.S. Cl. ................................ 514/12; 514/11; 514/13; 514/14; 530/387; 424/85
[58] Field of Search .............. 514/12, 11, 13, 14; 530/387; 424/85

[56] References Cited

PUBLICATIONS

Torti, F. M. et al., *Science*, 229: 867–869.
Beutler, B. et al., *Science*, 229: 869–871.
J. Exp. Med., vol. 154 (1981), 631–639.
Proc. Nat'l. Acad. Sci., 79, 912–916 (1982).

*Primary Examiner*—Delbert R. Phillips
*Attorney, Agent, or Firm*—Kate H. Murashige; Albert P. Halluin

[57] ABSTRACT

A method for controlling weight by suppressing the normal metabolism of adipose tissue is disclosed. Administration of tumor necrosis factor (TNF) or a pharmaceutical composition containing it results in suppression of anabolism of adipose cells.

12 Claims, 5 Drawing Figures

```
   1 CACACCCTGACAAGCTGCCAGGCAGGTTCTCTTCCTCTCACATACTGACCCACGGCTCCA

61 CCCTCTCTCCCCTGGAAAGGACACCATGAGCACTGAAAGCATGATCCGGGACGTGGAGCT
                           METSerThrGluSerMETIleArgAspValGluLeu

121 GGCCGAGGAGGCGCTCCCCAAGAAGACAGGGGGGCCCCAGGGCTCCAGGCGGTGCTTGTT
     AlaGluGluAlaLeuProLysLysThrGlyGlyProGlnGlySerArgArgCysLeuPhe

181 CCTCAGCCTCTTCTCCTTCCTGATCGTGGCAGGCGCCACCACGCTCTTCTGCCTGCTGCA
     LeuSerLeuPheSerPheLeuIleValAlaGlyAlaThrThrLeuPheCysLeuLeuHis

241 CTTTGGAGTGATCGGCCCCCAGAGGGAAGAGTCCCCCAGGGACCTCTCTCTAATCAGCCC
     PheGlyValIleGlyProGlnArgGluGluSerProArgAspLeuSerLeuIleSerPro

301 TCTGGCCCAGGCAGTCAGATCATCTTCTCGAACCCCGAGTGACAAGCCTGTAGCCCATGT
     LeuAlaGlnAlaValArgSerSerSerArgThrProSerAspLysProValAlaHisVal
                    1              6             11            16
 361 TGTAGCAAACCCTCAAGCTGAGGGGCAGCTCCAGTGGCTGAACCGCCGGGCCAATGCCCT
     ValAlaAsnProGlnAlaGluGlyGlnLeuGlnTrpLeuAsnArgArgAlaAsnAlaLeu
           21             26             31            36
 421 CCTGGCCAATGGCGTGGAGCTGAGAGATAACCAGCTGGTGGTGCCATCAGAGGGCCTGTA
     LeuAlaAsnGlyValGluLeuArgAspAsnGlnLeuValValProSerGluGlyLeuTyr
           41             46             51            56
 481 CCTCATCTACTCCCAGGTCCTCTTCAAGGGCCAAGGCTGCCCCTCCACCCATGTGCTCCT
     LeuIleTyrSerGlnValLeuPheLysGlyGlnGlyCysProSerThrHisValLeuLeu
              61             66            71            76
 541 CACCCACACCATCAGCCGCATCGCCGTCTCCTACCAGACCAAGGTCAACCTCCTCTCTGC
     ThrHisThrIleSerArgIleAlaValSerTyrGlnThrLysValAsnLeuLeuSerAla
              81             86            91            96
 601 CATCAAGAGCCCCTGCCAGAGGGAGACCCCAGAGGGGGCTGAGGCCAAGCCCTGGTATGA
     IleLysSerProCysGlnArgGluThrProGluGlyAlaGluAlaLysProTrpTyrGlu
           101            106            111           116
 661 GCCCATCTATCTGGGAGGGGTCTTCCAGCTGGAGAAGGGTGACCGACTCAGCGCTGAGAT
     ProIleTyrLeuGlyGlyValPheGlnLeuGluLysGlyAspArgLeuSerAlaGluIle
           121            126            131           136
 721 CAATCGGCCCGACTATCTCGACTTTGCCGAGTCTGGGCAGGTCTACTTTGGGATCATTGC
     AsnArgProAspTyrLeuAspPheAlaGluSerGlyGlnValTyrPheGlyIleIleAla
           141            146            151           156
 781 CCTGTGAGGAGGACGAACATCCAACCTTCCCAAACGCCTCCCCTGCCCCAATCCCTTTAT
     Leu...

841 TACCCCCTCCTTCAGACACCCTCAACCTCTTCTGGCTCAAAAAGAGAATTGGGGGCTTAG

901 GGTCGGAACCCAAGCTTAGAACTTTAAGCAACAAGACCACCACTTCGAAACCTGGGATTC

961 AGGAATGTGTGGCCTGCACAGTGAAGTGCTGGCAACCACTAAGAATTCAAACTGGGGCCT

1021 CCAGAACTCACTGGGGCCTACAGCTTTGATCCCTGACATCTGGAATCTGGAGACCAGGGA

1081 GCCTTTGGTTCTGGCCAGAATGCTGCAGGACTTGAGAAGACCTCACCTAGAAATTGACAC

1141 AAGTGGACCTTAGGCCTTCCTCTCTCCAGATGTTTCCAGACTTCCTTGAGACACGGAGCC

1201 CAGCCCTCCCCATGGAGCCAGCTCCCTCTATTTATGTTTGCACTTGTGATTATTTATTAT

1261 TTATTTATTATTTATTTATTTACAGATGAATGTATTTATTTGGGAGACCGGGGTATCCTG

1321 GGGGACCCAATGTAGGAGCTGCCTTGGCTCAGACATGTTTTCCGTGAAAACGGAGGCTGA

1381 ACAATAGGCTGTTCCCATGTAGCCCCCTGGCCTCTGTGCCTTCTTTTGATTATGTTTTTT

1441 AAAATATTATCTGATTAAGTTGTCTAAACAATGCTGATTTGGTGACCAACTGTCACTCAT

1501 TGCTGAGGCCTCTGCTCCCCAGGGAGTTGTGTCTGTAATCGGCCTACTATTCAGTGGCGA

1561 GAAATAAAGGTTGCTTAGGAAAGAA
```

FIG. 1

FIG. 2 TNF INHIBITS EXPRESSION OF CLONE 28 RNA

4,684,623

USE OF TUMOR NECROSIS FACTOR AS A WEIGHT REGULATOR

REFERENCE TO GOVERNMENT GRANT

This invention was made with Government support under grant no. GM 25821, awarded by the National Institutes of Health. The Government has certain rights in this invention.

CROSS-REFERENCE TO RELATED APPLICATION

This application is a continuation-in-part of copending U.S. patent application Ser. No. 730,367, filed May 2, 1985.

TECHNICAL FIELD

The invention relates to control of lipid metabolism using tumor necrosis factor (TNF). Specifically, the invention relates to a method of controlling obesity by administration of TNF.

BACKGROUND ART

Control of obesity has become a problem in developed cultures, despite the specter of hunger that often dominates portions of the less technologically advanced world. The litany of less-than-successful approaches which have been used in an attempt to control excess body weight is undoubtedly familar to most. Solutions range from reduced food consumption to often indiscriminate use of pharmaceuticals designed primarily for other purposes, but which appear to have a side effect of somewhat murky mechanism to result in weight loss. In short, there remain millions of people who wish to reduce their body weight without deprivation and without risking unpleasant and perhaps unhealthy side effects.

Of course, not all weight loss is necessarily desirable. Indeed, the weight loss attributable to the chronic catabolic state, referred to as cachexia, developed in the course of infections and malignancies is a handicap to recovery and is often directly fatal. In general, however, cachexia is thought to be a normal response to infection, and is undesirable only when permitted to proceed without proper control. The catabolism is characterized by a net breakdown of lipids in adipose cells, and it has been surmised that this undesirable balance is at least in part a result of failure of the cells to synthesize adequate amounts of lipogenic enzymes.

A crude protein extract from the media of endotoxin-stimulated macrophages, designated "cachectin", has been shown to induce indicia of cachexia in tissue culture (Torti, F., et al., Science (1985) 229: 867–869), and antibodies raised against it have been shown to protect mice from some of the effects of E. coli lipopolysaccharide endotoxin (Beutler, B., et al., ibid, pp. 869–871).

It has now been shown that tumor necrosis factor (TNF) specifically alters the characteristics of adipocytes in tissue culture in a manner thought to model at least part of the cachexia process. Later work has indicated that cachectin and native TNF, which was originally obtained from the sera of endotoxin-treated mice, and which is now available in recombinant form, have the same primary structure. Accordingly, TNF is a useful material for control of weight by stimulating this catabolic reaction under controlled conditions and under circumstances where such stimulation is desirable. It is also possible to control undesirable weight loss by neutralizing TNF.

DISCLOSURE OF THE INVENTION

The invention provides a defined pharmaceutical, tumor necrosis factor (TNF), which is capable of stimulating the physiological state associated with cachexia. The control of weight in adipose persons is thereby effected using a material which simulates a natural physiological response to infection under conditions where such simulation can be regulated and controlled.

Accordingly, in one aspect, the invention relates to a method for controlling obesity by administration of TNF. In another aspect the invention relates to controlling cachexia in cancer or infectious disease patients by providing antibodies to neutralize TNF. In other aspects, the invention relates to pharmaceutical compositions useful for weight reduction which contain TNF as an active ingredient, and to immunoglobulin compositions useful in neutralizing TNF.

BRIEF DESCRIPTION OF THE DRAWINGS

FIG. 1 shows the nucleotide sequence encoding human mature TNF and the deduced amino acid sequence.

FIG. 2 shows the accumulation of adipose-inducible mRNAs in maturing adipose cells and the regulation of synthesis of such mRNA in the presence and absence of TNF.

MODES OF CARRYING OUT THE INVENTION

A. Definitions

Figure 4A:
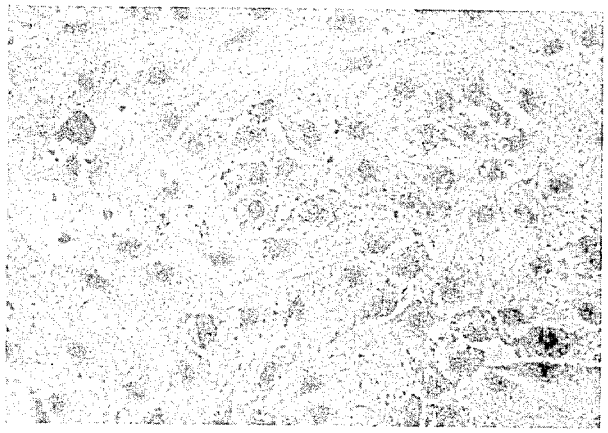
FIGS. 4A and 4B are photographs of mature adipose cells with and without TNF.

As used herein, "tumor necrosis factor" (TNF) refers to an amino acid sequence typified by that shown in FIG. 1, which is capable of selective cytotoxicity against tumor cells. The sequence of FIG. 1 is derived from a human cDNA, but TNF encoded by other mammalian species may exhibit the required activity as well. Retrieval and deduction of this sequence is described in detail in U.S. Ser. No. 760,661, filed July 30, 1985, assigned to the same assignee, and incorporated herein by reference. (See also, Wang, et al., Science (1985) 228:149.)

A TNF amino acid sequence, to fit the definition herein, must be active in the in vitro cytotoxicity assay based on the continuous murine connective tissue cell line L-929 as described hereinbelow. It is recognized that this definition of TNF activity is not precisely the same as that set forth in the disclosure coining this term by Carswell, et al. Proc Natl Acad Sci (USA) (1975) 72:3666. However, this activity as confirmed by the in vitro cytotoxicity assay against human tumor cells provides sufficient assurance of utility that qualification as a tumor necrosis factor for humans using this assay is justified; cytotoxicity against L-929 generalizes to human tumors. It is also expected that there is a substantial overlap between factors active in the specified cytotoxicity assay and the in vivo assay outlined by Carswell.

The TNF protein of the invention, depending on the pH of its environment if suspended or in solution, or of its environment when crystallized or precipitated if in solid form, may be in the form of pharmaceutically acceptable salts or may be in neutral form. The free amino groups of the protein are, of course, capable of forming acid addition salts with, for example, inorganic acids such as hydrochloric, phosphoric, or sulfuric acid; or with organic acids such as, for example, acetic glycolic, succinic, or mandelic acid. The free carboxyl groups are capable of forming salts with bases, including inorganic bases such as sodium, potassium, or calcium hydroxides, and such organic bases as piperidine, glucosamine, trimethylamine, chloine, and caffeine. In addition, the protein may be modified by combination with other biological materials such as lipids and saccharides, or by side chain modification such as acetylation of amino groups, phosphorylation of hydroxyl side chains, or oxidation of sulfhydryl groups. All of these modifications are included within the scope of the definition, so long as the TNF activity is retained.

Finally, it is understood that the primary amino acid sequence shown in FIG. 1 is only illustrative and that similar sequences result in proteins which have substantially equivalent or enhanced activity as compared to that set forth in FIG. 1. These modifications may be deliberate, for example, as obtained through site-directed mutagenesis, or may be accidental such as those obtained through mutation in hosts which are TNF producers. All of these modifications are included as long as TNF activity, as above-defined, is retained.

For example, it has been found that a mutein lacking the first four amino acids at the N-terminus of the sequence shown in FIG. 1 (Val-Arg-Ser-Ser) has a specific activity several fold higher than the TNF of the structure shown. (See U.S. Ser. No. 760,661, filed July 30, 1985, cited above). Accordingly, the definition of TNF specifically includes this truncated form. In addition, muteins lacking the N-terminal ten or less amino acids have similarly enhanced activity, and it appears that deletions of up to 10 amino acids from the N-terminus do not destroy, but, in fact, enhance biological activity.

Therefore, the definition of TNF herein specifically includes proteins having an amino acid sequence substantially equivalent to that shown in FIG. 1, but lacking 1-10 of the amino acids at the N-terminal sequence as shown in that figure.

U.S. Ser. No. 698,939, filed Feb. 7, 1985, assigned to the herein assignee and incorporated herein by reference, discloses cysteine-depleted muteins of the TNF of FIG. 1. In general, neutral amino acid replacements of the crysteine at position 69 or 101 or both result in active TNF proteins. Neutral amino acid replacements include ala, ser, val and the like, preferably ser. These muteins can also be modified to obtain truncated forms which retain TNF activity and may have enhanced specific activity in vitro and in vivo.

As to notation, for convenience, when particular peptides are specified, the protein having the amino acid sequence numbered 1-157 in FIG. 1 will be used as a reference and designated, perhaps arbitrarily, mTNF (mature TNF). All other specific proteins having homology with mTNF and showing TNF biological activity will be referred to as "muteins" of mTNF and will be denoted as to their differences from mTNF using the numbering of residues shown in the figure. For example, muteins which have substitutions for cysteine at position 69 will be denoted using the substituted residue and the position number, e.g., peptides having a serine in place of the cysteine at position 69 are designated $ser_{69}$ TNF. Muteins which lack, for example, three N-terminal amino acids as compared to the protein shown in FIG. 1 will be designated $\nabla 3TNF$. Where both of the foregoing alterations are made, the mutein is designated $\nabla 3ser_{69}TNF$.

Particularly preferred embodiments of the TNF of the inventions include $\nabla 2ser_{69}TNF$, $\nabla 2ser_{101}TNF$, $\nabla 2ser_{69}ser_{101}TNF$, and the corresponding $\nabla 3$, $\nabla 4$, $\nabla 5$, $\nabla 6$, $\nabla 7$, $\nabla 8$, $\nabla 9$ and $\nabla 10$ cysteine depleted muteins. Particularly preferred are $\nabla 8ser_{69}TNF$, $\nabla 8ser_{101}TNF$, $\nabla 8ser_{69}ser_{101}$ and $\nabla 4ser_{69}TNF$, $\nabla 4ser_{101}TNF$ and $\nabla 4ser_{69}ser_{101}TNF$.

Not all muteins of mTNF are recombinantly or deliberately produced. Indeed, native HL-60 cell secreted TNF has minor differences from mTNF in the known portions of the primary structure, although both proteins exhibit TNF activity. Specifically, the deduced sequence of FIG. 1 has an additional pair of serine residues following the serine at position 3 as compared to HL-60 derived TNF before resuming the homology shown between positions 4-12 of the HL-60 derived protein and positions 6-14 of the deduced sequence. In addition, positions 13 and 14 of the HL-60 derived protein are Val-Ser; the corresponding positions 15 and 16 of the deduced sequence are His-Val.

B. Modes of Preparation

The TNF useful in the method of the invention can most conveniently be prepared using recombinant methods. Detailed descriptions of ways to produce recombinant TNF are set forth in U.S. Ser. No. 661,026 Oct. 15, 1984), Ser. No. 670,360 (Sept. 11, 1984), Ser. No. 698,939 (Feb. 7, 1985), Ser. No. 730,696 (May 2, 1985), and Ser. No. 760,661 (supra), all incorporated by reference. In this regard, various DNA sequences enconding TNF have been deposited with the American Type Culture Collection, Rockville, MD. These DNA sequences include those contained in pE4 which harbors the human cDNA insert (ATCC #39894); pAW711 which is an expression vector suitable for procaryotes encoding the TNF of FIG. 1 (ATCC #39918) and pAW736, an expression vector encoding the $\nabla 4$ mutein of mTNF (ATCC #53092). Vectors suitable for expression of other TNF muteins ($\nabla 10$, $\nabla 9$, $\nabla 6$, $\nabla 7$, and $\nabla 8$) are deposited as ATCC Nos. 53161, 53162, 53163, 53164, and 53165, respectively.

In addition to recombinantly produced materials, the TNF may be extracted from natural source such as human or other mammalian tissues, or from human or other mammalian derived cell lines. The source of the protein is, of course, immaterial to the practice of the invention except as it may affect specific dosage levels and administration regimes required.

C. Formulaion and Mode of Administration

To effect the desired lipid mobilization resulting from administration of TNF, the active ingredient may be formulated using a variety of acceptable excipients as is known in the art. Typically, the TNF will be administered by injection, either intraperitoneally or intravenously. However, by suitable formulations, it may be possible to obtain compositions which may be topically or orally administered, or which may be capable of transmission across mucous membranes.

Depending on the nature of the composition and the mode of administration, the compositions may be in solid or liquid form. For solid compositions, conventional carriers include, for example, phamaceutical grades of mannitol, lactose, starch, talcum, cellulose, magnesium carbonate and the like. The TNF may be formulated as a suppository using, for example, polyalkylene glycols as carrier. Liquid compositions can be prepared by dissolving or dispersing the TNF and optional adjuvants in a carrier such as, for example, water, saline, aqueous dextrose, and so forth. If desired, the composition may also contain minor amounts of nontoxic auxiliary substances such as wetting or emulsifying agents, pH buffering agents, and the like. Actual methods of preparing dosage forms are known or will be apparent to those of the art. The composition will, in any event, contain a quantity of TNF in an amount effective to effect the desired lipid mobilization.

A preferred method of administration of this protein is by injection, most commonly intraperitoneally or intravenously. The injectable can be prepared either as a liquid solution or a suspension or in a solid form susceptible to reconstitution.

The dosage and mode of administration will, of course, depend on the level of lipid mobilization desired, the nature of the subject, and the judgment of the medical practitioner. In general, however, effective dosages are in the range of 0.02-2 µg of TNF per kg of body weight per day for so long as administration is required. This range represents, of course, a broad estimate as the above-listed factors are of great importance in determining optimal dosage levels.

In that aspect of the invention which relates to neutralization of TNF in cachexic patients, a preferred embodiment to neutralize the activity of TNF employs polyclonal or monoclonal antibodies. These neutralizing antibodies are preferably used as adjunctive treatment with other cytotoxic drugs in cancer patients. For example, the patient might be administered methotrexate to kill the tumor followed by the antibody preparation to neutralize TNF to prevent weight loss.

Polyclonal antibodies are prepared to TNF using conventional procedures by injecting purified TNF into a convenient host, such as rabbits or mice, and harvesting high titer sera. Preparation of monoclonal compositions generally follows the now well known procedure of Köhler and Milstein.

D. Example

The following examples are intended to illustrate, but not limit the invention.

Preparation A: Preparation of Cachectin

Cachectin was used as a control in the following examples. It is prepared from the conditioned media of endotoxin stimulated macrophages, as described by Kawakami, M., et al., *Proc Natl Acad Sci (USA)* (1982) 79:912; Pekala, P. H., et al., (ibid 1983) 80:2743.

Example 1

Effect of TNF on Adipose-Inducible mRNA Levels

An in vitro model for the study of the abnormal metabolism of cachexia has been developed using a stable adipogenic cell line (TA1) as disclosed in Chapman, A. B., *J Biol Chem* (1984) 259:15548-15555. These cells develop an adipocyte morphology approximately 3 days after confluence in tissue culture monolayers, and show, in parallel with this morphology, the expression of several genes. Certain proteins and enzymes are present only in differentiated adipocytes and are not present or are present only at undetectable levels in the undifferentiated precursors. These proteins are considered to be products of "adipose-inducible genes" and of their intermediate mRNAs.

Genes for which expression is first evident after differentiation have been identified. They are designated clones 1, 10, 28, 47, and GPD (Chapman, A. B., et al., supra). Their expression is apparently due to transcriptional activation.

Therefore, one measure of the impact of compounds on adipocytes is their effect on the levels of adipose-inducible mRNA.

In this assay, the above stable adipogenic cell line, TA1, was cultured from preconfluence to 24 days after confluence. TNF, prepared by culturing pAW711 transformed *E. coli* and inducing the expression of TNF as described in Ser. No. 760,661 (supra) was added to the cell cultures from preconfluence to 6 days thereafter.

In more detail, TA1 cells, which are derived from 5-azacytidine treatment of 10 T1/2C18 cells (Resnikof, C., et al., *Cancer Res* (1973) 33:3231-3238; Taylor, S. M., et al., *Cell* (1979) 17:771-779) were grown in Eagle's basal medium supplemented with 10% heat inactivated fetal calf serum. $10^{-6}$M dexamethasone was present in media for the first 3 days after confluence, and 5 µg/ml bovine insulin for the first 6 days after confluence.

Recombinant TNF (10-30 ng/ml) was first added to preadipocyte cultures 2 days prior to confluence. (Addition of this amount inhibits 90% of lipoprotein lipase activity in cultured adipocytes.) Cells were fed with resupplementation of TNF at day 0 (confluence) and at day 3. Cells were harvested at day 6.

Total RNA was isolated by the method of Chirgwin, J. M., et al., *Biochemistry* (1979) 18:5294-5299, and applied to nitrocellulose in a dot-blot apparatus (BRL). Nick translated cDNA clones of adipose-inducible genes (designated clones 1, 10, 47, and glycerol phosphate dehydrogenase (GDH)) were used to probe the filters under hybridization conditions described in Chapman, A. B., et al., *J Biol Chem* (1984) (supra). Filters were washed and exposed to XAR 5 film at −70° C. with an intensifying screen.

The results are shown in the left column of FIG. 2, labeled "Steady State". It is clear from these results that TNF treatment prevents accumulation of adipose-inducible mRNA. These results are comparable to those obtained when 10 µl/ml cachectin is used in place of TNF.

Lipid accumulation was also completely inhibited by cachectin or TNF, and TA1 cell cultures treated with these compounds have been maintained for as long as 23 days without the appearance of neutral lipid evident by oil red O staining. However, on removal of cachectin or TNF from the medium, adipocyte morphology returns, as does the expression of adipose-inducible genes. It was also shown that TNF or cachectin treatment of preadipocyte cultures does not affect cell growth or viability as determined by cell counting and by $^3$H-thymidine incorporation, as well as by trypan blue exclusion and the clonal growth assay of Ham, R. G., et al., *Cell CultureMethods for Molecular and Cellular Biology*, Barnes, N.Y. (1984) 1:3-21.

Accordingly, the results show that either cachectin or TNF suppresses the total amount of adipose inducible mRNA available in adipocytes or preadipocytes, without influencing negatively the remainder of the cell's metabolism.

Example 2

Inhibition of Transcription

That mRNA accumulation inhibition is transcriptionally regulated was shown by nuclear transcription assays performed as described by Vannice, et al., *Proc Natl Acad Sci (USA)* (1984) 81:4241–4245 and by Israel, J., et al., *J Biol Chem* (1984) 259:5400–5402, as modified by Knight, et al. (submitted) for adipose cells.

At each data point, cells cultured and treated as in Example 1 were chilled to 4° C. and the media were aspirated and washed with phosphate buffered saline. One ml of hypotonic buffer (20 mM Tris/HCl, pH 8, 4 mM $MgCl_2$, 6 mM $CaCl_2$, 0.5 mM dithiothreitol) was added to the plates. After 5 min, 1 ml of lysis buffer (0.6M sucrose, 0.2% NP 40, and 0.5 mM dithiothreitol) was added and the cells were scraped from the tissue culture dishes. After Dounce homogenization, nuclei were pelleted at 500 g, washed once in resuspension buffer, repelleted, and then resuspended in buffer containing 0.4 mM each of ATP, CTP, GTP, 10% glycerol, and 10 μg/ml BSA. The nuclei were incubated with an α-32P-UTP (600 Ci/mmol) at a concentration of 2 μCi/ml for 40 min at 45° with gentle shaking.

RNA was harvested from the nuclei as described by Smith, et al., *Cell* (1978) 15:615–626 as modified by Knight, et al. (supra) and hybridized to linearized cDNAs which had been applied to nitrocellulose filters and baked for 2 hr at 80° C. in a vacuum oven. Filter prehybridization and hybridization conditions were those of Friedman, R. L., et al., *Cell* (1984) 38:745–755, and hybridizations were performed for 3 days at 42° C. with about $15 \times 10^6$ cpm per reaction mixture applied in 150 μl volume to dots of linearized single-stranded adipose cDNAs for clone 28, and the cDNA encoding β-actin and the non-corresponding neutral plasmid pEMBL were used as comparisons. The β-actin cDNA clone was a gift of P. Gunning and L. Kedes.

The results are shown in the righthand column of FIG. 2. The four data points are preconfluence (PC). 4 hours after TNF addition, 24 hours after TNF addition, and "control", which represents TA1 untreated with TNF. Columns A and E are respectively the β-actin and pEMBL comparison dot probes; column 28 represents the clone 28 dot probe. These results show that the transcription system contained in the nucleus is suppressed with respect to the coding sequences for clone 28, which is characteristic of adipose cells, but unaffected with respect to the encoding sequences for actin. Similar results were obtained when the TA1 cells were treated with 10 μl/ml cachectin. Therefore, TNF, like cachectin, operates directly on the genome to suppress transcription of adipose-related sequences, but does not disrupt other gene function.

Example 3

Effect of TNF on Mature Adipose Cells

Figure 3:
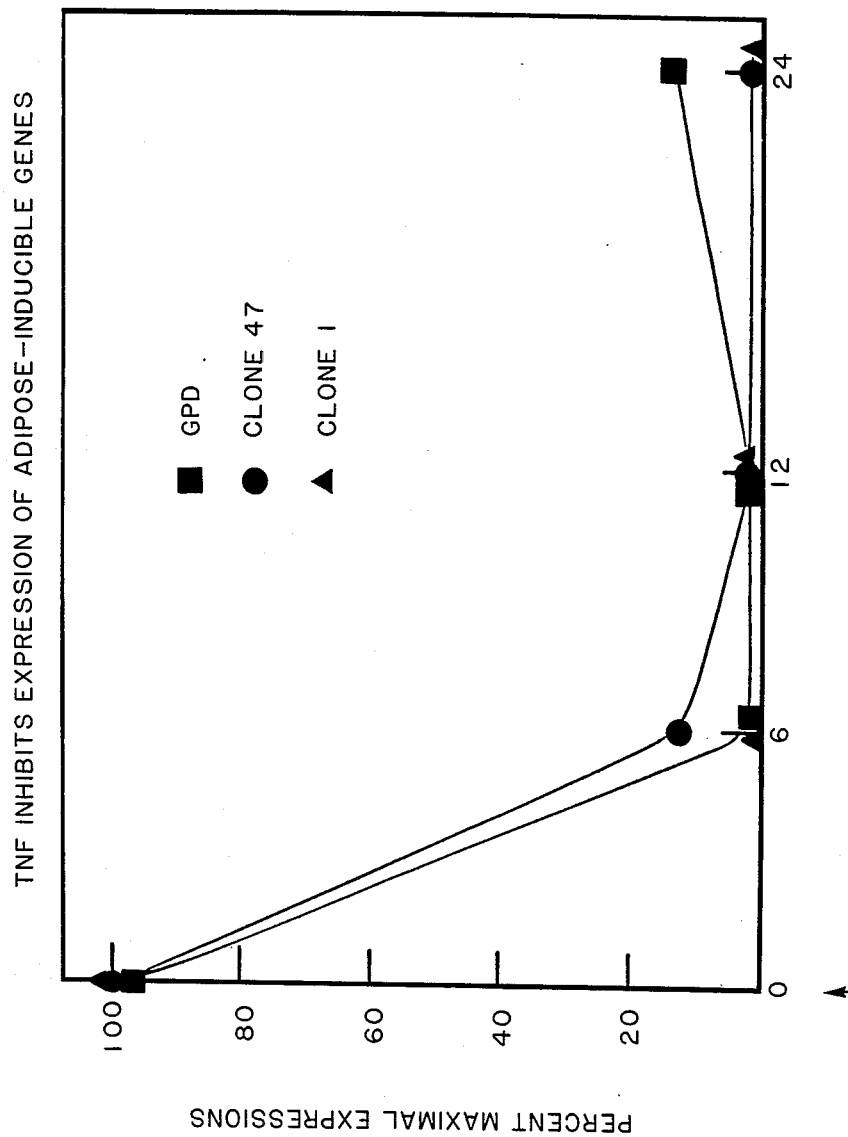
FIG. 3 shows the depression of expression of adipose stimulated genes by TNF.

Since in adult mammals, adipocytes undergo little or no proliferation, it was desirable to study the effect of TNF on mature adipose cells. A sample of 10–30 ng/ml of TNF was added to day 6 adipocyte TA1 cultures differentiated as described in Example 1. Total RNA was isolated from the cells at various times after TNF exposure and applied to nitrocellulose with a dot blot apparatus. Filters were probed with cDNAs for GPD, clone 47, and clone 1, washed, autoradiographed, and scanned using a Hoeffer GS300 densitometer attached to a reporting integrator. The points obtained were normalized for differences in amount of applied RNA using a cDNA probe made to total cellular RNA. FIG. 3 shows that maximal expression of GPD, or clones 1 or 47 is severely inhibited after the first 6 hours in the presence of TNF. Results for cachectin are similar.

Northern blots probed with clone 47 at various times after the TNF treatment showed that the RNA hybridizable to this clone diminished quickly after TNF administration. For these analyses, 12 μg total RNA was brought to a final concentration of 2.2M formaldehyde, 30% formamide, 10 mM $NaH_2PO_4$, pH 7 and heated for 15 min at 56°. Samples were electrophoresed in a 1% agarose formaldehyde gel with a final concentration of 2.2M formaldehyde, 20 mM MOPS, pH 7.0, 5.0 mM sodium acetate and 1 mM EDTA. Gels were washed in distilled water for 3 min, followed by two 30 min washes in 10 mM $NaPO_4$, pH 7.4 and 1 mM EDTA before transferring to cellulose, and hybridization with linearized cDNA from clone 47. Again, cachectin-treated cells showed similar results.

Figure 4B:
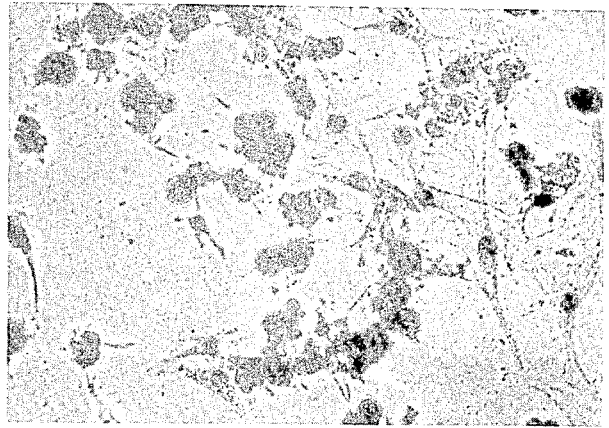

It was also shown that after 4–6 days of TNF exposure, most cells lose their neutral lipid. When 10–30 ng/ml TNF is added, 70%–80% of cells are laden with large lipid droplets; 6 days later less than 10% of cells have identifiable triglycerides on oil red O stains. These results are shown in FIGS. 4B and 4A, which represent untreated and TNF-treated cells, respectively. The oil red O stain has almost entirely disappeared from the cells of FIG. 4A.

Comparison of these results with those shown in FIG. 3 shows that alterations in adipose specific RNAs due to TNF treatment occur more rapidly than lipid mobilization. By 6–24 hr after addition of TNF to mature TA1 lymphocytes, more than a 90% decrease in said RNAs is observed; several days are required for this to be reflected in a decrease in lipid content.

Addendum: Cytotoxic Assay Procedure

Definition of a protein as TNF depends on its activity in the L-929 assay. This assay is therefore described here.

The L-929 assay system is an improved convenient in vitro assay which permits rapid measurement of TNF activity. Its degree of correlation with the invivo tumor necrosis assay of Carswell is, at present, unknown; however, as it utilizes murine tumor cells specifically, the correlation is expected to be high. The protein designated lymphotoxin in EPO publication no. 0100641 also gives activity in this assay. The assay is similar in concept to that disclosed in U.S. Pat. No. 4,457,916 which used murine L-M cells and methylene blue staining. However, the L-929 assay has been shown to correlate (for HL-60-derived TNF) with human tumor cell line cytotoxicity.

In the L-929 assay system herein, L-929 cells are prepared overnight as monolayers in microtiter plates. The test samples are diluted 2-fold across the plate, UV irradiated, and then added onto the prepared cell monolayers. The culture media in the wells are then brought to 1 μg/ml actinomycin D. The plates are allowed to incubate 18 hr at 37° C. and the plates are scored visually under the microscope. Each well is given a 25, 50, 75 or 100% mark signifying the extent of cell death in the well. One unit of TNF activity is defined as the reciprocal of the dilution at which 50% killing occurs.

In addition, a more sensitive version of this assay was developed that monitors the release of $^{35}$S labeled peptides from prelabeled cells, when treated with the test sample and actinomycin D. This version of the assay can be used to quantitate potency, e.g., to evaluate the relative potency of oocyte translated material. Briefly, actively growing L-929 cultures are labeled with $^{35}S$ methionine (20 μCi/ml) for 3 hr in methionine-free media supplemented with 2% dialyzed fetal calf serum. The cells are then washed and plated into 96 well plates, incubated overnight, and treated the next day with 2-fold dilutions of test samples and 1 μg/ml actinomycin D. The cultures were then incubated at 37° C. for 18 hr. 100 μl supernatant aliquots from each well were then transferred onto another 96 well plate, acid (TCA) precipitated, and harvested onto glass fiber filters. The filters were washed with 95% ethanol, dried and counted. An $NP_{40}$ detergent control is included in every assay to measure maximum release of radioactivity from the cells. The percent $^{35}S$ release is then calculated by the ratio of the difference in count between the treated cells and untreated controls divided by the difference between $NP_{40}$ treated cells and untreated controls, i.e., by the ratio:

$$\% \text{ release} = \frac{\text{sample} - \text{cell control}}{NP_{40} - \text{cell control}} \times 100.$$

Higher TNF potency results in higher values of this ratio.

Summary

The foregoing examples indicate that TNF is successful in suppressing the metabolism of adipose cells. This activity is also demonstrable for cachectin; see Torti, F. M., et al. (supra). Accordingly, TNF prevents the expression of genes responsible for producing enzymes important in storing fat and is useful in controlling weight.

We claim:

1. A method of effecting weight reduction by administering to a subject in need of such treatment an amount of tumor necrosis factor (TNF) effective to cause said weight reduction or a pharmaceutical composition containing said amount, wherein said TNF is the mTNF having the amino acid sequence shown in FIG. 1 or a mutein thereof, wherein said mutein is selected from the group consisting of $\nabla 1 TNF$, $\nabla 2$-, $\nabla 3$- . . . through $\nabla 10 TNF$;

$ser_{69}TNF$, $\nabla 1ser_{69}TNF$, $\nabla 2ser_{69}TNF$ . . . through $\nabla 10ser_{69}TNF$;

$ser_{101}TNF$, $\nabla 1ser_{101}TFN$, $\nabla 2ser_{101}TNF$ . . . through $\nabla 10ser_{101}TNF$;

$ser_{69}ser_{101}TNF$, $\nabla 1ser_{69}ser_{101}TNF$, $\nabla 2ser_{69}ser_{101}TNF$ . . . through $\nabla 10ser_{69}ser_{101}TNF$; and a mutein having the sequence of amino acids 21–157 of FIG. 1 with the N-terminal sequence Val-Arg-Ser-Arg-Thr-Pro-Ser-Asp-Lys-Pro-Val-Ala-Val-Ser-Val-Ala-Asn-Pro.

2. A method of suppressing adipose cell metabolism which comprises administering to a subject in need of such treatment an amount of TNF effective to suppress adipose cell metabolism or a pharmaceutical composition containing said amount, wherein said TNF is the mTNF having the amino acid sequence shown in FIG. 1 or a mutein thereof, wherein said mutein is selected from the group consisting of $\nabla 1 TNF$, $\nabla 2$-, $\nabla 3$- . . . through $\nabla 10 TNF$;

$\nabla 1ser_{69}TNF$, $\nabla 2ser_{69}TNF$ . . . through $\nabla 10ser_{69}TNF$;

$ser_{101}TNF$, $\nabla 1ser_{101}TNF$, $\nabla 2ser_{101}TNF$ . . . $\nabla 10ser_{101}TNF$;

$ser_{69}ser_{101}TNF$, $\nabla 1ser_{69}ser_{101}TNF$, $\nabla 2ser_{69}ser_{101}TNF$ . . . $\nabla 10ser_{69}ser_{101}TNF$; and a mutein having the sequence of amino acids 21–157 of FIG. 1, with the N-terminal sequence Val-Arg-Ser-Arg-Thr-Pro-Ser-Asp-Lys-Pro-Val-Ala-Val-Ser-Val-Ala-Asn-Pro.

3. The method of claim 1 wherein the TNF has an amino acid sequence substantially equivalent to that of FIG. 1 (mTNF).

4. The method of claim 1 wherein the TNF is recombinant TNF.

5. The method of claim 1 wherein the TNF is selected from the group consisting of $\nabla 1 TNF$, $\nabla 2$-, $\nabla 3$-, . . . $\nabla 10 TNF$.

6. The method of claim 1 wherein the TNF is selected from the group consisting of $ser_{69}TNF$, $\nabla 1ser_{69}TNF$, $\nabla 2ser_{69}TNF$, $\nabla 3$-, . . . $\nabla 10ser_{69}TNF$.

7. The method of claim 1 wherein the TNF is selected from the group consisting of $ser_{101}TNF$, $\nabla 1ser_{101}TNF$, $\nabla 2ser_{101}TNF$, $\nabla 3$-, . . . $\nabla 10ser_{101}TNF$.

8. The method of claim 1 wherein the TNF is selected from the group consisting of $ser_{69}ser_{101}TNF$, $\nabla 1ser_{69}ser_{101}TNF$, $\nabla 2ser_{69}ser_{101}TNF$, $\nabla 3$-, . . . $\nabla 10ser_{69}ser_{101}TNF$.

9. The method of claim 1 wherein the TNF is selected from the group consisting of $\nabla 8ser_{69}TNF$, $\nabla 8ser_{101}TNF$, and $\nabla 8ser_{69}ser_{101}TMF$.

10. The method of claim 1 wherein the TNF is selected from the group consisting of $\nabla 4ser_{69}TNF$, $\nabla 4ser_{101}TNF$, and $\nabla 4ser_{69}ser_{101}TNF$.

11. The method of claim 1 wherein the TNF has the N-terminal sequence:
    Val-Arg-Ser-Arg-Thr-Pro-Ser-Asp-Lys-Pro-Val-Ala-Val-Ser-Val-Ala-Asn-Pro.

12. A method of controlling undesirable weight loss which comprises administering to a subject in need of such control a neutralizing amount of antibodies specific for the TNF of claim 1 or a pharmaceutical composition thereof.

* * * * *

UNITED STATES PATENT AND TRADEMARK OFFICE
CERTIFICATE OF CORRECTION

PATENT NO. : 4,684,623

DATED : Aug. 4, 1987

INVENTOR(S) : James W. Larrick, Gordon M. Ringold, David F. Mark, Leo S. Lin, Frank M. Torti It is certified that error appears in the above-identified patent and that said Letters Patent is hereby corrected as shown below:

On the title page assignee should read

-- (73) Assignees: The Board of Trustees of the Leland Stanford Junior University, Stanford; Cetus Corporation, Emeryville, both of Calif. --

Signed and Sealed this

Fifteenth Day of March, 1988

Attest:

DONALD J. QUIGG

Attesting Officer

Commissioner of Patents and Trademarks